United States Patent [19]

DiMaggio, Jr.

[11] 4,137,299

[45] Jan. 30, 1979

[54] BIOLOGICAL STAINING COMPOSITION AND STAINING METHOD

[76] Inventor: Joseph P. DiMaggio, Jr., 283 E. Main St., Bergenfield, N.J. 07621

[21] Appl. No.: 570,020

[22] Filed: Apr. 21, 1975

[51] Int. Cl.$^2$ .................. D06P 1/00; G01N 1/30; G01N 33/16
[52] U.S. Cl. .................. 424/3; 8/3; 8/25; 8/93; 424/7; 424/8
[58] Field of Search .......... 424/3, 7, 8; 8/3, 25, 8/93, 94.1, 94.11, 127

[56] References Cited

U.S. PATENT DOCUMENTS

| | | | |
|---|---|---|---|
| 3,677,690 | 7/1972 | Kalopissis | 8/93 |
| 3,873,272 | 3/1975 | Wakefield | 424/7 |
| 3,928,554 | 12/1975 | Hirschfield | 424/3 |

OTHER PUBLICATIONS

Miller, A Textbook of Clin. Path., Williams & Wilkins, Baltimore, 7th Ed. 1966.
Cosmetic Bull. Brij. Surfactants, Atlas Chem. Ind., Wilmington, Del., 1961.
Lillie, Histopath. Technic & Pract. Histochem., McGraw-Hill, N.Y., 3rd Ed. 1965, pp. 585–588.

*Primary Examiner*—Anna P. Fagelson
*Attorney, Agent, or Firm*—David A. Jackson

[57] ABSTRACT

A composition for use in staining biological samples such as blood smears which comprises a stain component and a buffer component, said components prepared in separate solutions, wherein each of said solutions contains a small quantity of a polyethylene oxide adduct of a long-chain, saturated aliphatic ether non-ionic surfactant. The surfactant is added to each component after the preparation of its respective solution. The composition is particularly useful in automated slide staining machines.

7 Claims, No Drawings

BIOLOGICAL STAINING COMPOSITION AND STAINING METHOD

BACKGROUND OF THE INVENTION

The present invention relates generally to the field of biological stains and particularly to stains employed in blood sample analysis.

In the preparation of biological samples for analysis, certain natural and synthetic dyes have been used to stain tissues, cells, cell components and other microscopical specimens in order to facilitate their examination with the aid of a high-powered microscope. These dyes stain the materials and bring out color differences between cell components and their background or between different parts of the substrate. Stains are thus employed when it is desired to differentiate chromatically one part of a specimen from another. Because of the variation in the composition of the respective parts of the specimen, attempts to completely stain the specimen must include treatment with one or more different dyes, either in the same or separate solutions. For example, blood smears are usually stained by treatment with a methylene blue-eosinate dissolved in methanol, of which Wright's stain is an example. As Wright's stain contains three different types of dyes, i.e., an acid dye, a basic dye, and a neutral dye, cellular elements responsive to the difference in chemical structure are simultaneously stained.

Though stains such as Wright's stain have been used for some time with reasonable accuracy, there has developed an increasing need for stains possessing greater flexibility and sensitivity to slight variations in the pathological condition of the specimen. Particularly in the instance of the acid dyes, a certain lack of discrimination is evident in the failure of the dye to penetrate certain cellular inclusions such as mitochondria and cytoplasmic granules. Also, even when the desired elements are stained, they are often severely damaged or crenated. It is thus difficult to know the actual condition of the specimen, or to accurately diagnose the patient's condition.

With the advance of medical science bringing to attention new maladies possessing more subtle symptoms, greater sensitivity is required in all aspects of analysis. This need is especially felt in the area of microscopic examination, and the preparation of samples therefor.

SUMMARY OF THE INVENTION

In accordance with the present invention, a staining composition is prepared which provides increased, more accurate staining of biological samples such as blood smears. The composition of the present invention comprises a staining component and a buffer component, both of said components prepared in separate solutions, wherein each of said solutions further contains a small quantity of a non-ionic surfactant selected from the group consisting of the polyethylene oxide adducts of long-chain, saturated aliphatic ethers. The surfactant may be added to the solutions in an amount up to about one percent by volume.

The method of the present invention comprises providing the stain and buffer components in their respective solutions, to each of which the aforenoted surfactant is then added. In the instance where a blood smear stain is desired, Wright's stain powder may be placed in solution with acetone-free methyl alcohol, and a rinse solution may be provided in addition to the stain and buffer components.

The stain compositions of the present invention enable samples to be faithfully stained without destruction and crenation of the cells. Also, cellular details are identified which were not previously discernable.

Stains prepared by the method of the invention are less time-consuming to formulate, and attain a higher level of purity. Particulate contaminants are all but eliminated, and specimens are more easily stained. Ease of operation and uniformity of stain quality are especially noticeable when the compositions are employed in automated staining machines.

Accordingly, it is a principal object of the present invention to provide a biological staining composition which possesses a wider diagnostic capability than conventional stain compositions.

It is another object of the present invention to provide a composition as aforesaid which fully stains every element of the biological specimen without deleterious effect to its structure.

It is a further object of the present invention to provide a staining composition comprising a stain solution and a buffer solution to each of which has been added a small quantity of a non-ionic surfactant comprising a polyethylene oxide adduct of a long-chain, saturated aliphatic ether.

It is a still further object of the present invention to provide a method for preparing the staining composition as aforesaid which comprises adding said non-ionic surfactant to each of said solutions after their respective preparations.

It is yet a further object of the present invention to provide a composition and method as aforesaid which are useful with an automated staining machine.

Further objects and advantages will become apparent from a consideration of the ensuing description.

DETAILED DESCRIPTION

In accordance with the present invention, the foregoing objects and advantages are readily obtained.

A composition is disclosed for use in the staining of biological samples such as blood smears which comprises a stain component and a buffer component which are each prepared in separate solutions, and a non-ionic surfactant added to each of said solutions in a small quantity. The surfactant comprises a polyethylene oxide adduct of a long-chain, saturated aliphatic ether, and in a preferred embodiment, comprises polyethylene oxide 23 lauryl ether, which is commercially available from Atlas Chemical Industries, Ltd., as Brij 35. The surfactant is added to the solutions in an amount ranging up to about 1 percent by volume, and is preferably added in amounts of about 0.5 percent by volume of a 30 percent solution.

The compositions which may be prepared in accordance with the invention include most of the biological stains which employ dyes that are dissolved in a solvent, and thus applies to acid and basic dyes, as well as direct and mordant dyes. A particular stain composition comprises a dye placed in an alcohol diluent, which is useful for blood smear analysis. The particular dye is a mixture of an acid dye and a basic dye to provide a neutral dye as well, and comprises methylene blue and eosin. This mixture is better known as Wright's stain, and, as such, has long been employed in blood smear staining. Together with this stain, a buffer solution is usually prepared which comprises a phosphate salt prepared in a solution the pH of which is adjusted to a value of from 6.4 to 7.0.

In the present procedure of its use, the solution of Wright's stain in methyl alcohol is applied to the specimen either alone or together with the buffer solution. If applied alone, the stain is left on the specimen for from about 2 to 4 minutes, after which the buffer is applied to aid the staining reaction and both are then allowed to remain for an additional time ranging from about 2 to 6 minutes to complete staining. If the stain and buffer are applied together, a waiting period of from about 2 to 4 minutes is observed, after which an equal volume of buffer alone is then added. A further wait of from 4 to 6 minutes is observed, after which staining is complete.

The completely stained specimen is then rinsed with a solution which may comprise ordinary tap water or the buffer (for maintenance of pH). In an embodiment of the present invention, a rinse solution is employed which comprises acetonefree methyl alcohol in a 20 percent by volume aqueous solution with sterile, particle and bacteria-free water. After rinsing, the specimen is dried under ambient conditions and is then ready for examination.

The above procedure possesses several drawbacks, as noted earlier herein. The stain tends to bypass certain cellular elements and other elements are observed to deteriorate and incur extensive damage from its use. Though the precise cause of the above difficulties is not known, applicant believes that they stem, in part, from the effects that the water component of the stain composition has on the specimen. Specifically, free molecules of water appear to prevent complete stain uptake by the cells, while, at the same time, cause the cells to collapse or crenate, and thus deteriorate or destroy certain cellular elements. Naturally, the result of the above is that the specimen no longer accurately represents the condition of the organism, blood, etc., and, additionally, vital components thereof are either partially or totally unstained.

It has been unexpectedly observed that the above phenomena have been controlled and prevented by the addition of the aforenoted quantity of non-ionic surfactant to the stain and buffer solutions, respectively. The surfactant is theorized to maintain the water in suspension and to thus prevent its influence over cellular staining and integrity. Samples treated with the composition of the present invention are fully stained and possess no cellular damage.

As noted earlier, the method of the present invention generally comprises adding the non-ionic surfactant to the separate solutions of the stain and the buffer after their preparation, in an amount ranging up to about 1 percent by volume of a 30 percent solution, and preferably in the case of the above blood smear stain, in an amount of about 0.5 percent by volume. In the latter embodiment, however, it should be noted that the rinse solution does not and should not contain any surfactant, as this may affect the integrity of the prepared specimen.

The invention comprising both the composition and its method of preparation will be presented in more detail in the following illustrative examples.

EXAMPLE I

In this example a staining composition for use in blood smear analysis was prepared. A quantity of Wright's stain powder comprising methylene blue and eosin was dissolved in a volume of absolute acetone-free methyl alcohol, in a mixing ratio of 3 grams of powder per liter of alcohol. The resulting solution was then placed in incubation for a period of one month at room temperature (20°–25° C.). During this time, the solution was maintained in darkness and was agitated once daily by shaking or the like. After the completion of incubation, the solution was filtered into a clean container through high quality, fine filter paper. If any residue was noted after filtration, the solution was refiltered in like manner. When filtration was completed, the surfactant comprising a 30 percent solution of Brij 35 was added in an amount of about 0.5 ml. for every 100 ml of solution.

The buffer solution was prepared with a phosphate salt such as sodium dihydrogen phosphate and sterile, bacteria- and particle-free water in a ratio of 1 gram of salt per liter of water. Though sodium dihydrogen phosphate is illustrated, other salts are contemplated which would serve in the aforenoted capacity, and the invention should not, accordingly, be limited thereto. The particular water set forth is not limiting, but has been found to minimize subsequent contamination of the specimen. After suitable mixing, the buffer solution is completed by the addition of a 30 percent solution of Brij 35 in the same ratio of that employed with the stain solution, above.

Finally, and as earlier noted, a rinse solution is prepared which comprises a 20 percent by volume aqueous solution of absolute acetone-free methyl alcohol in sterile, bacteria- and particle-free water.

The preparation of the stain comprises, in the above example, an incubation period of one month which is significantly reduced from conventional preparation of this dye, which can take up to nine months in some instances. A much quicker incubation period may be employed, as set forth in Example II, below.

EXAMPLE II

A stain composition identical in content to that of Example I was prepared. Upon completion of initial mixture, the solution was incubated in a dark container for a period of 24 hours, with frequent agitation, and at a temperature ranging at about 98° F. Following incubation, the solution was filtered, and the Brij 35 solution then added. The resulting solution functioned comparably with the stain solution prepared in Example I.

The remaining components such as the buffer and the rinse, were identical in composition and preparation with those set out in Example I.

The above compositions may be employed in the same general manner as conventional stain compositions of this kind. Staining results will, however, be clearly superior as noted earlier. The composition finds particular utility in employment in automated slide staining machines.

Throughout the specification, all percentages not stated otherwise are to be interpreted as percentage by weight.

This invention may be embodied in other forms or carried out in other ways without departing from the spirt or essential characteristics thereof. The present invention is therefore to be considered as in all respects illustrative and not restrictive, the scope of the invention being indicated by the appended claims, and all changes which come within the meaning and range of equivalency are intended to be embraced therein.

What is claimed is:

1. A stain composition for use in staining biological samples which comprises a mixture of a first component comprising Wright's stain solution prepared from Wright's stain powder in solution in absolute, acetone-free methyl alcohol in the ratio of 3 grams of said powder per liter of said methyl alcohol, and a second component comprising a 30% solution of a non-ionic surfactant comprising a polyethylene oxide (23) lauryl ether, said second component present in an amount up to about one percent by volume of said first component.

2. The stain composition of claim 1 wherein said second component is present in an amount of about 0.5 percent by volume of said first component.

3. In the method of staining a biological sample which comprises applying to said sample a stain composition comprising Wright's stain in solution in methyl alcohol, permitting said stain composition to remain in contact with said samples for a time sufficient to enable said sample to become stained thereby, thereafter applying an equal quantity of a buffer solution comprising an aqueous solution of a phosphate salt, and maintaining said buffer solution in contact with said samples for from four to six minutes, and rinsing said sample and drying said sample under ambient conditions, the improvement wherein said stain composition and said buffer solution each respectively contain up to about one percent by volume of a 30% solution of a non-ionic surfactant comprising a polyethylene oxide (23) lauryl ether.

4. The method of claim 3 wherein said stain composition includes a quantity of said buffer solution therewith.

5. The method of claim 3 wherein said non-ionic surfactant is present in an amount of about 0.5 percent by volume.

6. The method of claim 3 wherein said stain composition is maintained in contact with said sample for a period of from two to four minutes.

7. The method of claim 3 wherein said buffer solution is adjusted in pH to within a range of from 6.4 to 7.0.